United States Patent
Hine et al.

(10) Patent No.: US 11,248,973 B2
(45) Date of Patent: Feb. 15, 2022

(54) INSERTION AND WITHDRAWAL FORCE MEASUREMENT SYSTEM

(71) Applicant: C.R. Bard, Inc., Murray Hill, NJ (US)

(72) Inventors: Robert M. Hine, Covington, GA (US); John David Sangiorgio, Athens, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 640 days.

(21) Appl. No.: 15/434,900

(22) Filed: Feb. 16, 2017

(65) Prior Publication Data
US 2018/0231426 A1    Aug. 16, 2018

(51) Int. Cl.
*G01L 5/00* (2006.01)
*G01N 3/06* (2006.01)
*A61B 90/00* (2016.01)

(52) U.S. Cl.
CPC .................. *G01L 5/0033* (2013.01)

(58) Field of Classification Search
CPC .................. A63F 13/06; A63F 13/285; A63F 2300/1037; A63F 2300/8017; G01B 21/04; G01B 5/008; G06F 3/011; G06F 3/0346; G06F 3/038; G06F 2203/015; G06F 3/016; G06F 3/03545; G06F 3/0383; G09B 9/28; G05G 2009/0474; G05G 9/047; A61B 5/6885; A61B 17/3403; A61B 2017/00243; A61B 2017/00477; A61B 2034/301; A61B 17/3476; A61B 2090/065; A61B 2090/064; A61B 2017/003; A61M 25/01; G01M 1/045; G01M 1/16
See application file for complete search history.

(56) References Cited

U.S. PATENT DOCUMENTS

| 3,795,140 | A | * | 3/1974 | Nishihara | ........... G01F 23/0038 |
| | | | | | 73/309 |
| 6,981,945 | B1 | | 1/2006 | Sarvazyan et al. | |
| 8,052,621 | B2 | | 11/2011 | Wallace et al. | |
| 8,915,908 | B2 | | 12/2014 | Privitera et al. | |
| 9,458,905 | B2 | * | 10/2016 | Battey | ..................... F16F 1/041 |
| 9,618,069 | B2 | * | 4/2017 | DeStories | ............ B25J 15/0028 |

(Continued)

FOREIGN PATENT DOCUMENTS

| DE | 19645334 | 5/1998 |
| EP | 2848911 | 3/2015 |

(Continued)

OTHER PUBLICATIONS

Zoarski, et al., "Performance Characteristics of Microcatheter Systems in a Standardized Tortuous Pathway." AJNR Am J Neuroradiol 19:1571-1576, Sep. 1998.

(Continued)

*Primary Examiner* — Brandi N Hopkins
(74) *Attorney, Agent, or Firm* — Dorton & Willis, LLP; Ryan Willis

(57) ABSTRACT

A force measuring system for devices comprising: (a) a tortuous conduit operatively coupled to a transducer; and, (b) a computer communicatively coupled to the transducer, the computer programmed to utilize signals output from the transducer to calculate forces acting on the transducer, the computer programmed to support a graphical user interface for displaying the calculated forces.

22 Claims, 8 Drawing Sheets

(56) References Cited

U.S. PATENT DOCUMENTS

| | | | |
|---|---|---|---|
| 2007/0186603 A1* | 8/2007 | Hogendoorn | B21D 9/00 |
| | | | 72/31.04 |
| 2009/0260834 A1* | 10/2009 | Henson | E21B 17/206 |
| | | | 166/385 |
| 2010/0000328 A1 | 1/2010 | Mahmoud | |
| 2010/0292566 A1 | 11/2010 | Nagano et al. | |
| 2012/0290000 A1* | 11/2012 | Bacher | A61B 17/29 |
| | | | 606/209 |
| 2015/0202423 A1 | 7/2015 | Adenusi et al. | |

FOREIGN PATENT DOCUMENTS

| | | |
|---|---|---|
| EP | 2908112 | 8/2015 |
| JP | 5171535 | 1/2013 |
| WO | 2016097140 | 6/2016 |
| WO | PCT/US18/15167 | 5/2018 |

OTHER PUBLICATIONS

European Patent Office, Extended European Search Report in EP 18754326.9, dated Nov. 26, 2020.
Japan Patent Office, Notice of Reasons for Refusal in JP 2019-543757, dated Jul. 6, 2021.

\* cited by examiner

INSERTION AND WITHDRAWAL FORCE MEASUREMENT SYSTEM

INTRODUCTION TO THE INVENTION

The present disclosure is directed to devices, systems, and methods to determine and compare insertion and withdrawal forces of various devices that may include, without limitation, medical devices. The instant disclosure also includes a software interface with an associated hardware testing component to provide graphical and numerical data concerning the insertion and withdrawal forces generated as a function of time, path distance, and/or path boundary material.

It is a first aspect of the present invention to provide a force measuring system for medical devices comprising: (a) a tortuous conduit operatively coupled to a transducer; and, (b) a computer communicatively coupled to the transducer, the computer programmed to utilize signals output from the transducer to calculate forces acting on the transducer, the computer programmed to support a graphical user interface for displaying the calculated forces.

In a more detailed embodiment of the first aspect, the transducer comprises a load cell. In yet another more detailed embodiment, a first portion of the transducer is mounted to a base, and a second portion of the transducer is mounted to a sled repositionably mounted to the base. In a further detailed embodiment, the tortuous conduit is removably mounted to the sled, and the sled includes a pair of upstanding arms that cooperatively engage a retention cap to selectively mount the tortuous conduit to the sled. In still a further detailed embodiment, the sled is at least one of pivotally repositionable and slidably repositionable with respect to the base. In a more detailed embodiment, the sled is pivotally repositionable with respect to the base, and a lever operatively couples the sled and the base and provides for the sled to pivot with respect to the base. In a more detailed embodiment, the lever comprises a plurality of levers. In another more detailed embodiment, at least one of the sled and the base includes a cavity into which the lever is at least partially inserted, the lever includes a pair of hollowed areas configured to receive cylindrical pins, the sled includes a sled opening sized to receive a first one of the cylindrical pins, and the base includes a base opening sized to receive a second one of the cylindrical pins. In yet another more detailed embodiment, the sled is slidably repositionable with respect to the stationary base, and a slide operatively couples the sled and the stationary base and provides for the sled to slide with respect to the stationary base.

It is a second aspect of the present invention to provide a process for comparing insertion and withdrawal forces of devices, the process comprising: (a) inserting a first device into a tortuous conduit; (b) recording insertion data indicative of insertion forces applied to the first device traveling in a first direction in the tortuous conduit; (c) withdrawing the first device from the tortuous conduit; (d) recording withdrawal data indicative of withdrawal forces applied to the first device traveling in a second direction in the tortuous conduit, where the second direction is generally opposite the first direction; (e) repeating the foregoing steps by replacing the first device with a second device; and, (f) comparing the insertion data and withdrawal data between at least the first and second devices.

In a more detailed embodiment of the second aspect, the devices may be medical devices. In a further detailed embodiment of the second aspect, the tortuous conduit is rigidly mounted to a load cell, the load cell is configured to output signals having a magnitude proportional to a force applied to the tortuous conduit, and the load cell is communicatively coupled to a programmed computer utilizing the signals and calculating the insertion forces and calculating the withdrawal forces. In yet another more detailed embodiment, the programmed computer supports a graphical user interface, and the graphical user interface displays the insertion forces and the withdrawal forces. In a further detailed embodiment, the insertion forces include a maximum insertion force, the withdrawal forces include a maximum withdrawal force, the graphical user interface displays the maximum insertion force and the maximum insertion force as part of a graph depicting force as a function of time, and the graphical user interface displays a separate graph for the first device and a second device. In still a further detailed embodiment, the graphical user interface also displays the maximum insertion force separate from the graph, the graphical user interface also displays the maximum withdrawal force separate from the graph, and the graphical user interface displays a separate reading for the maximum withdrawal force and the maximum insertion force for the first device and a second device. In a more detailed embodiment, the insertion forces are displayed on the graphical user interface in real-time, and the withdrawal forces are displayed on the graphical user interface in real-time. In a more detailed embodiment, the graphical user interface includes a button to be clicked for initiating recordation of the insertion data, and the graphical user interface includes a button to be clicked for concluding recordation of the withdrawal data. In another more detailed embodiment, the button initiating recordation of the insertion data is the same as the button concluding recordation of the withdrawal data. In yet another more detailed embodiment, the graphical user interface includes a separate button initiating recordation of the insertion data for first device and a separate button for concluding recordation of the withdrawal data for the second device. In still another more detailed embodiment, the tortuous conduit is representative of a bodily conduit the first and second devices would traverse when used during a medical procedure. In yet another more detailed embodiment, the first and second devices comprise a first catheter and a second catheter.

It is a third aspect of the present invention to provide a force measuring system for devices comprising: (a) a tortuous conduit operatively coupled to a transducer; (b) a base; and, (c) a sled repositionably mounted to the base, where a first portion of the transducer is mounted to the base, and a second portion of the transducer is mounted to the sled.

In a more detailed embodiment of the third aspect, the transducer comprises a load cell. In yet another more detailed embodiment, the tortuous conduit is removably mounted to the sled, and the sled includes a pair of upstanding arms that cooperatively engage a retention cap to selectively mount the tortuous conduit to the sled. In a further detailed embodiment, the sled is at least one of pivotally repositionable and slidably repositionable with respect to the base. In still a further detailed embodiment, the sled is pivotally repositionable with respect to the base, and a lever operatively couples the sled and the base and provides for the sled to pivot with respect to the base. In a more detailed embodiment, at least one of the sled and the base includes a cavity into which the lever is at least partially inserted, the lever includes a pair of hollowed areas configured to receive cylindrical pins, the sled includes a sled opening sized to receive a first one of the cylindrical pins, and the base includes a base opening sized to receive a second one of the cylindrical pins. In a more detailed embodiment, the lever comprises a plurality of levers, each of the sled and the base includes a cavity into which the plurality of levers is at least partially inserted, and each of the plurality of levers includes a pair of hollowed areas configured to receive cylindrical pins. In another more detailed embodiment, each of the upstanding arms includes an arcuate depression configured to receive at least a portion of the tortuous conduit, and the retention cap includes an arcuate depression configured to receive at least a portion of the tortuous conduit. In yet another more detailed embodiment, the retention cap comprise a plurality of retention caps, a first of the plurality of retention caps cooperates with a first of the upstanding arms to sandwich the tortuous conduit therebetween, and a second of the plurality of retention caps cooperates with a second of the upstanding arms to sandwich the tortuous conduit therebetween. In still another more detailed embodiment, the first of the plurality of retention caps is selectively mounted to the first of the upstanding arms using a first threaded fastener, and the second of the plurality of retention caps is selectively mounted to the second of the upstanding arms using a second threaded fastener. In yet another more detailed embodiment, the sled is slidably repositionable with respect to the stationary base, and a slide operatively couples the sled and the stationary base and provides for the sled to slide with respect to the stationary base.

DETAILED DESCRIPTION

The exemplary embodiments of the present disclosure are described and illustrated below to encompass exemplary testing devices/systems, methods, displays, and outputs associated with the foregoing devices/systems. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
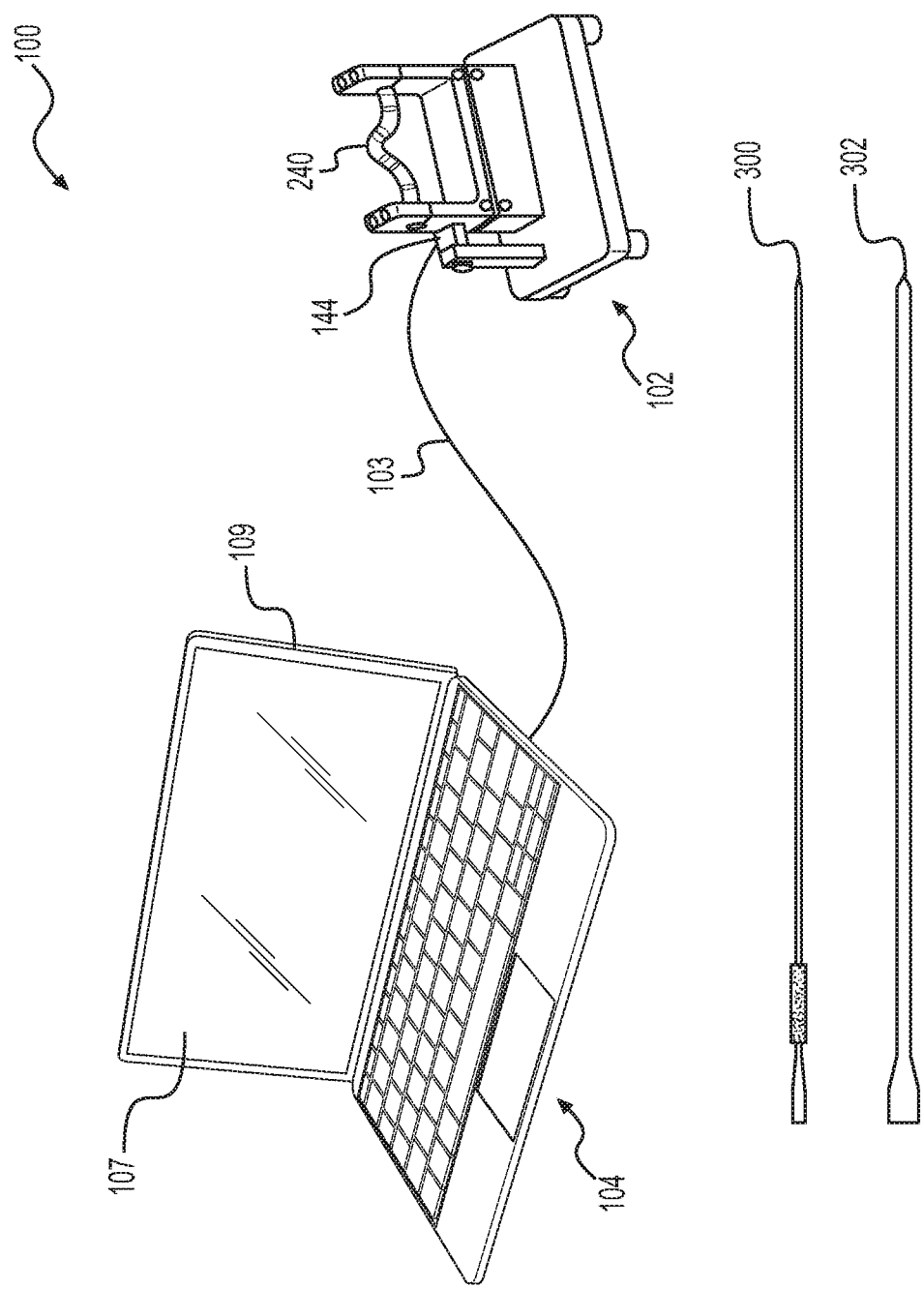
FIG. 1 is an elevated perspective view of an exemplary force analytic system in accordance with the instant disclosure.
Figure 2:
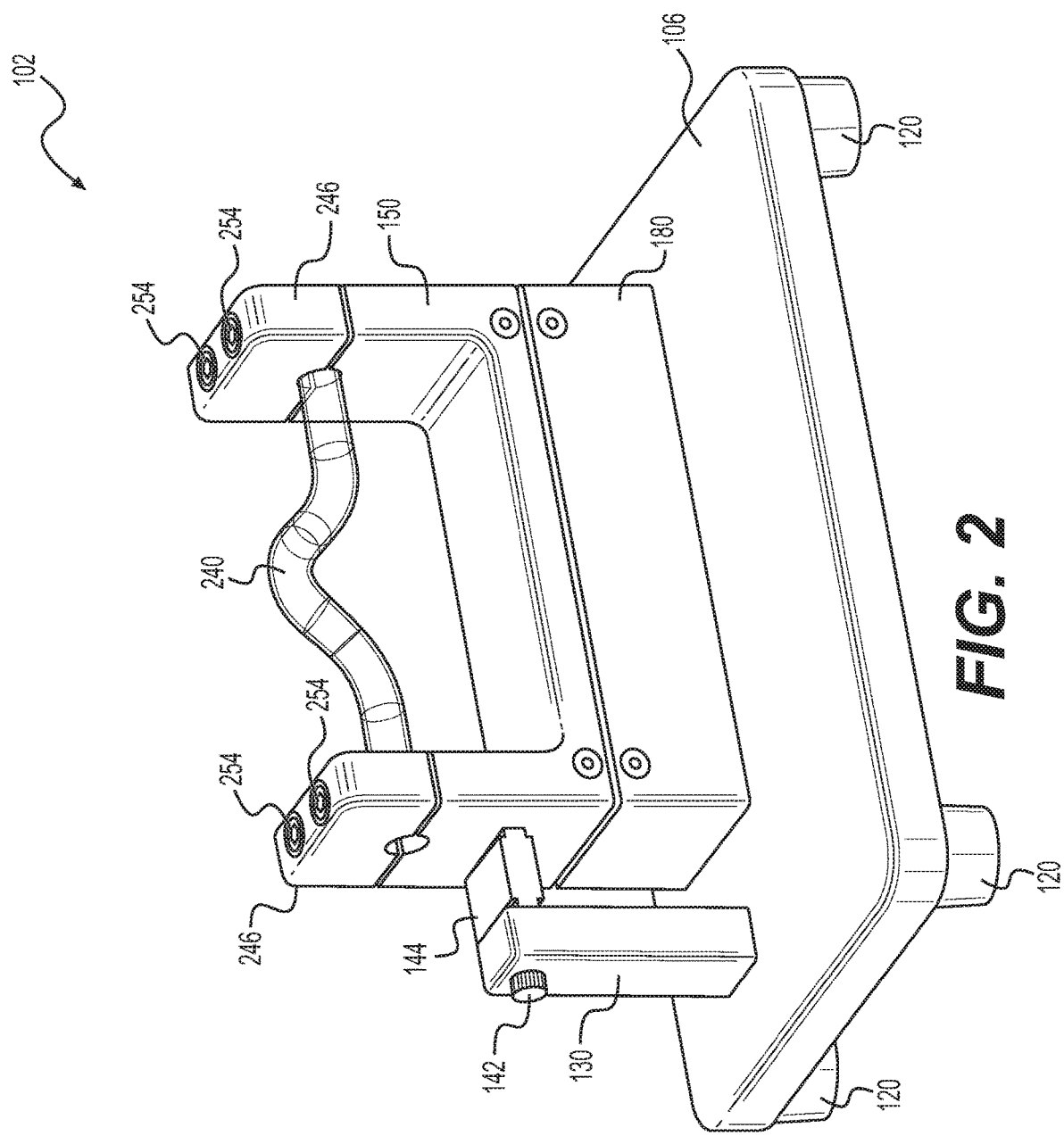
FIG. 2 is an elevated perspective view of an exemplary measuring device comprising part of the exemplary system of FIG. 1.
Figure 3:
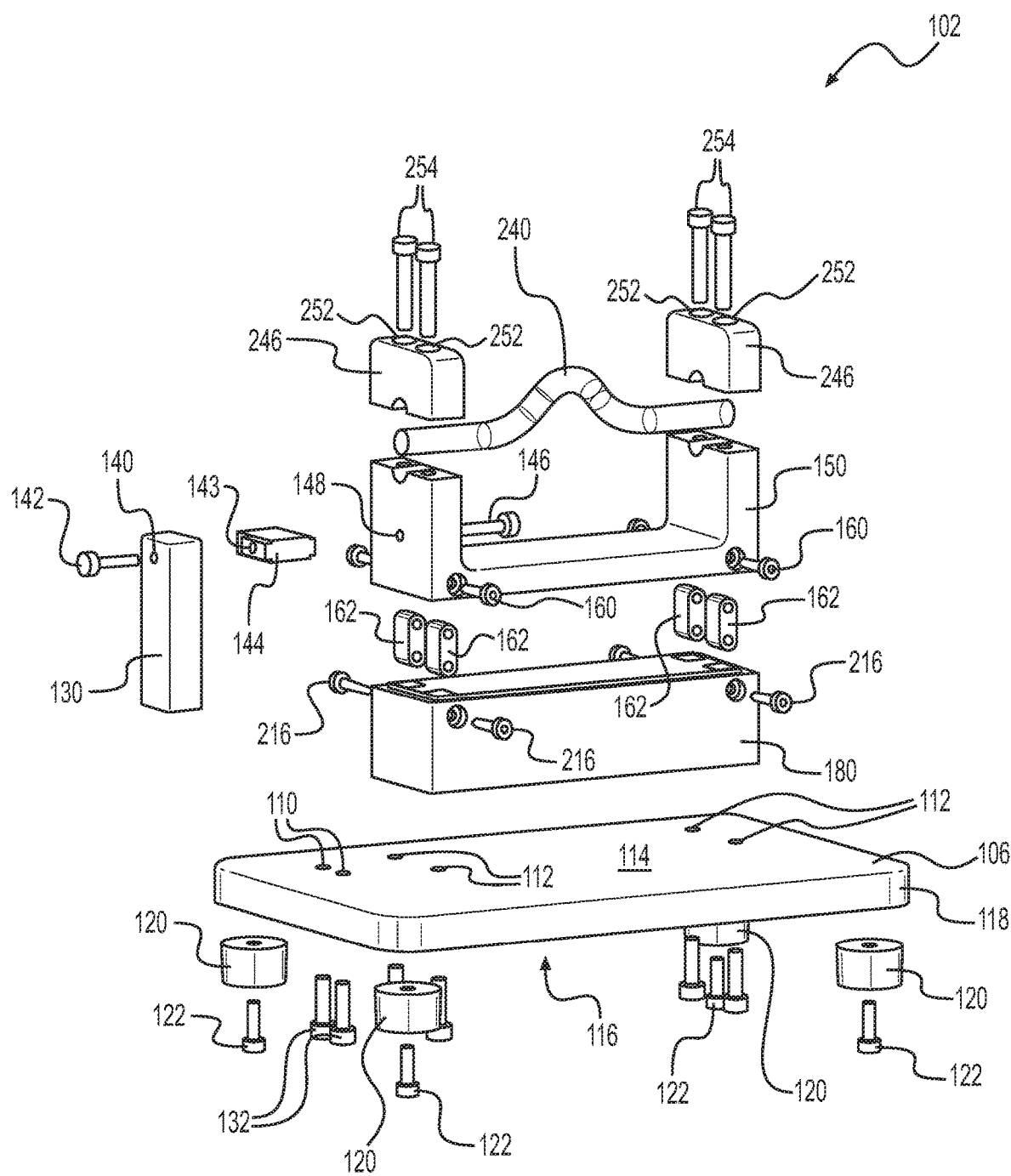
FIG. 3 is an exploded view, from an elevated perspective, of the exemplary measuring device of FIG. 2.
Figure 4:
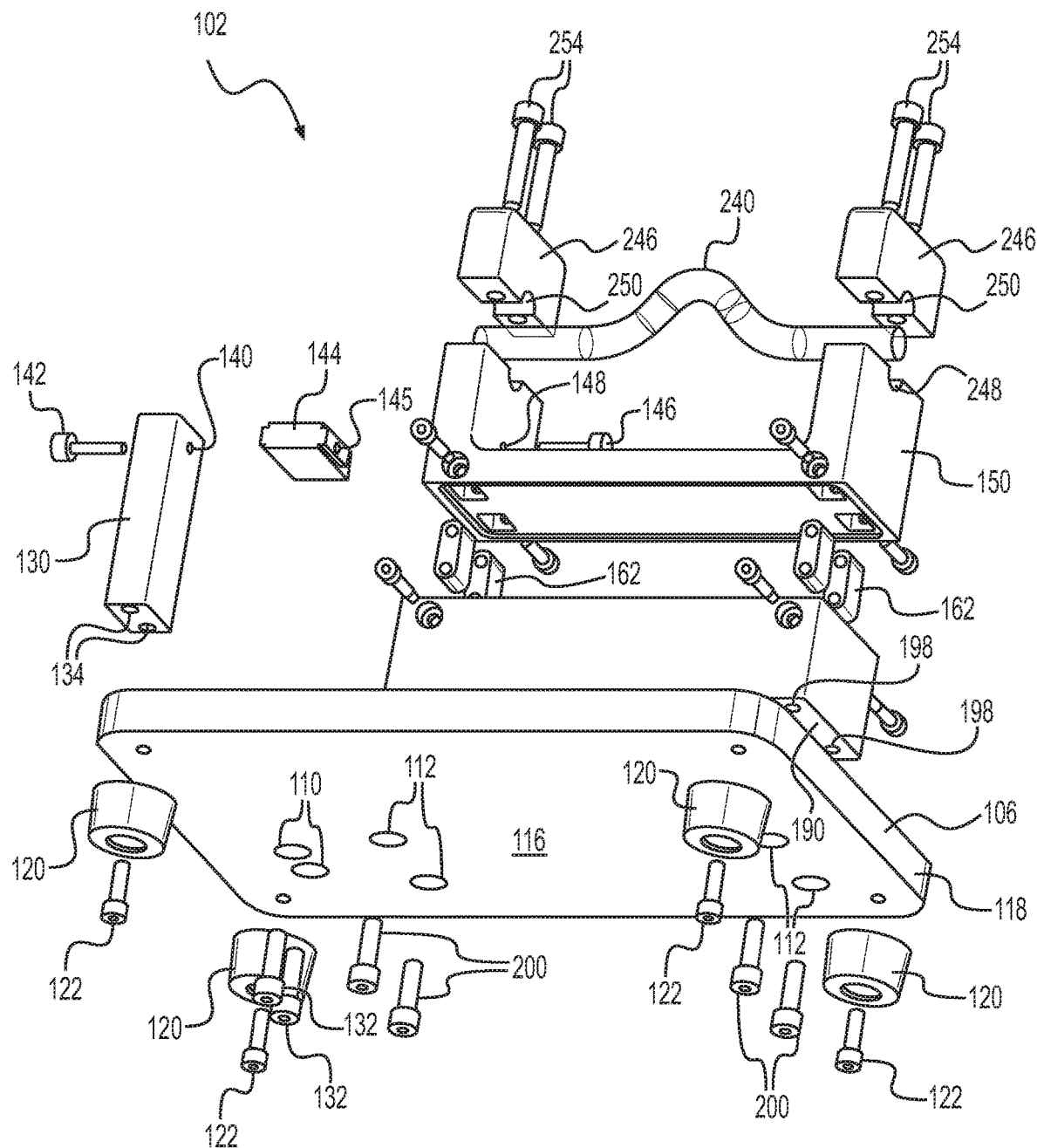
FIG. 4 is an exploded view, from a lowered perspective, of the exemplary measuring device of FIG. 2.
Figure 5:
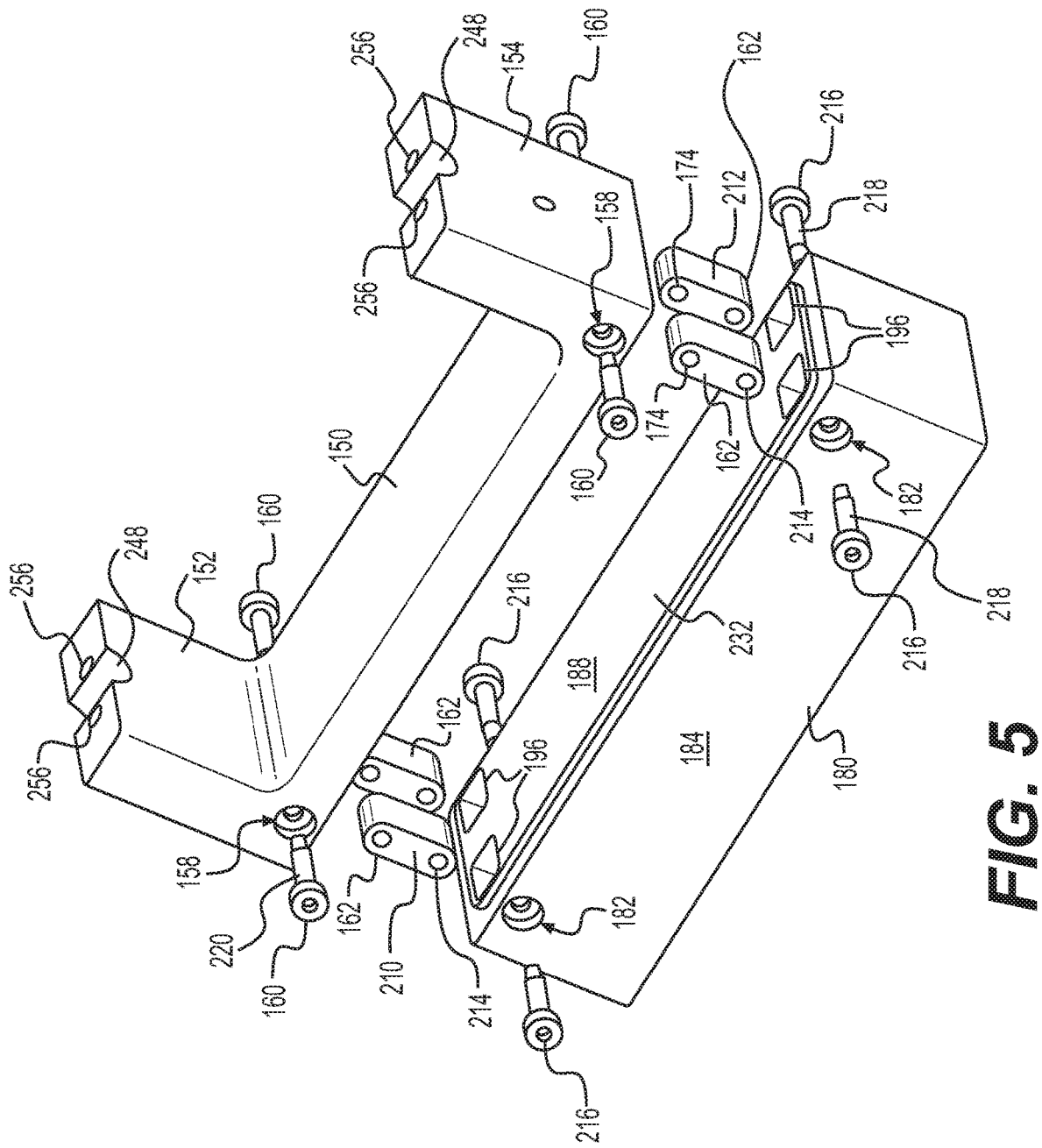
FIG. 5 is an exploded view of the sled, levers, baseplate, and fasteners comprising a part of the exemplary measuring device of FIG. 2.
Figure 6:
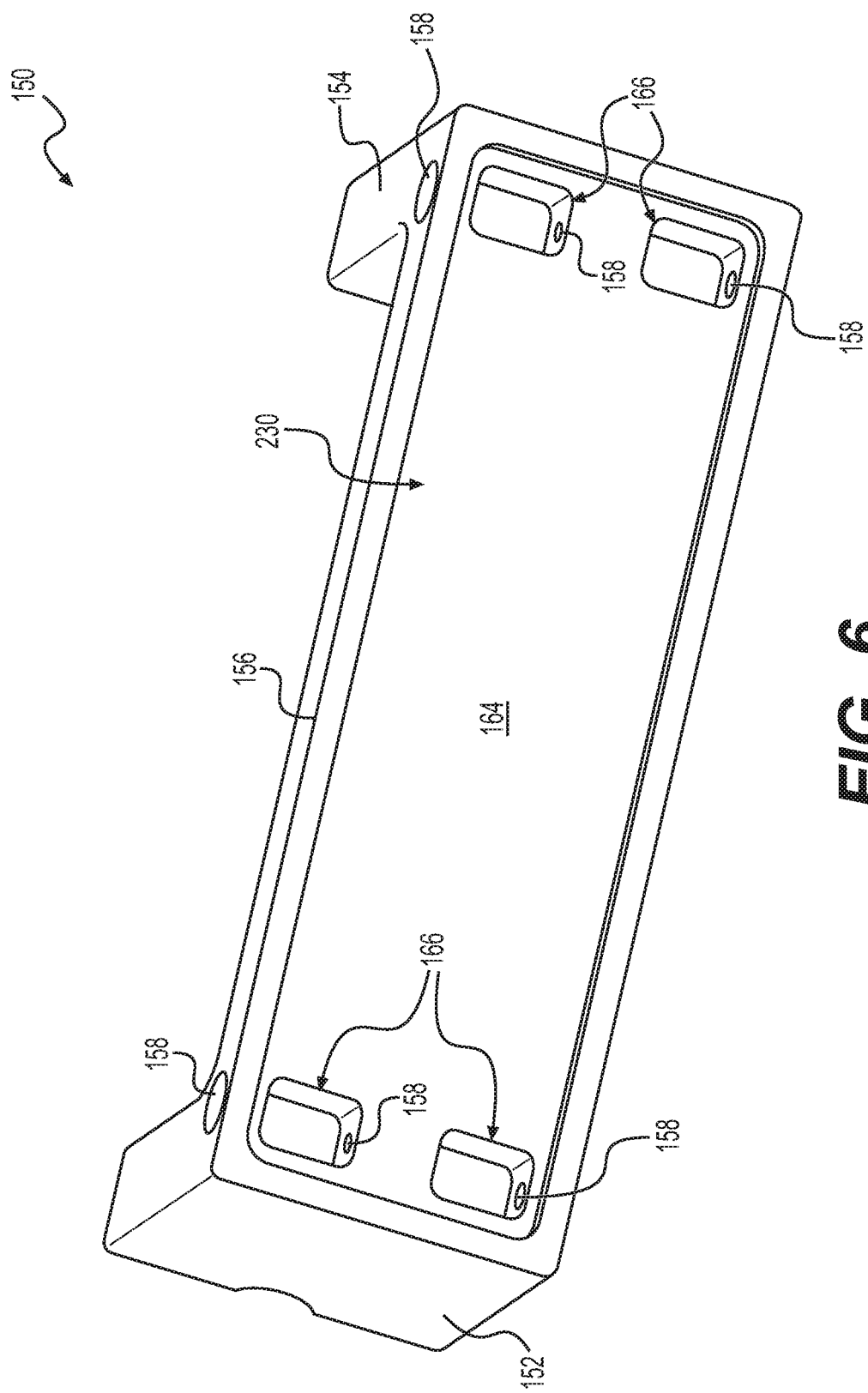
FIG. 6 is a lowered perspective view of the sled of FIG. 5.

Referencing FIG. 1, an exemplary force analytic system 100 includes a measuring device 102 communicatively coupled to a computer 104. The communicative coupling may be wired 103 or wireless between the computer 104 and the measuring device 102, both wired and wireless connections being well known to those skilled in the art and need not be discussed in greater detail for purposes of brevity.

Referring to FIGS. 2-6, the exemplary measuring device 102 comprises a platform 106 having a series of through holes 110, 112 extending between opposed top and bottom surfaces 114, 116. By way of example, the top and bottom surfaces 114, 116 are planar and bridged by a constant height circumferential surface 118 delineating a rounded, rectangular boundary. A plurality of feet 120 are mounted to the bottom surface 116 via individual fasteners 122 such as, without limitation, threaded screws. The feet 120 are positioned in proximity to, but inset with respect to, the four corners of the platform 106. In exemplary form, the feet 120 may embody a frustro-pyramidal shape and be formed of an elastomeric or polymer material. But it should also be noted that the feet 120 may embody any number of shapes and be fabricated from any number and variety of materials. In any event, the feet 120 are mounted to the platform 106 opposite the other components of the measuring device 102.

A vertical support 130 embodying a rectangular cuboid shape is mounted to the platform 106 by threaded fasteners 132 extending from the bottom surface 116, through two of the holes 110, and above the top surface 114. By way of example, the vertical support may be fabricated from a block of aluminum. In particular, a bottom face of the vertical support 130 includes a pair of threaded cavities 134 that are configured to receive portions of the threaded fasteners 132 that extend above the top surface 114 in order to secure the vertical support 130 to the platform 106. A dominant longitudinal dimension of the vertical support 130 extends perpendicularly with respect to the top surface 114 so that a mounting hole 140 extends parallel to the top surface 114 and perpendicular with respect to the cavities 134. In exemplary form, the mounting hole 140 is sized to receive a threaded fastener 142 that engages a corresponding cavity 143 of a load cell 144. An opposite side of the load cell 144 housing includes a second cavity 145 to receive a second threaded fastener 146 that extends through a passage 148 in a sled 150, thereby mounting the load cell to the sled. In this exemplary embodiment, the load cell 144 comprises a transducer creating electrical signals whose magnitude is directly proportional to the force applied to the load cell. Exemplary load cells 144 that may be used as part of the exemplary measuring device include, without limitation, the Mini Tension/Compression Force Sensor, MR04-2, commercially available from Mark-10 Corporation, 11 Dixon Avenue, Copiague, N.Y. 11726 USA.

In exemplary form, the sled 150 comprises a block U-shaped support, which may be fabricated from a solid block of aluminum, having a pair of towers 152, 154 extending perpendicularly away from opposing lateral ends of a connecting bridge 156. Proximate the corners of the bridge 156, where the bridge and towers 152, 154 meet, is a pair of through holes 158 configured to receive fasteners 160 to pivotally mount the sled to a series of pivot levers 162. In exemplary form, the through holes 158 extend perpendicular to the dominant longitudinal dimensions of the bridge 156 and the towers 152, 154. An underside surface 164, generally opposite the direction that both towers 152, 154 extend, includes four cavities 166, with each cavity configured to receive a portion of a respective pivot lever 162. In this exemplary embodiment, two of the four cavities 166 intersect a first of the through holes 158, while the other two of the four cavities 166 intersect a second of the through holes 158. In this fashion, a respective fastener 160 extends through a respective hole 158 and through a corresponding hole 174 of each of two of the pivot levers 162 in order to pivotally mount the sled 150 to the levers. And the pivot levers 162 are also pivotally mounted to a baseplate 180 secured to the top surface 114 of the plate 106.

It should be noted that the sled may alternatively be mounted to the baseplate using any number of structures that provide for movement between the sled and baseplate. By way of example, the pivot levers 162 may be replaced by a roller slide, a roller conveyor, ball bearings, magnetic levitation, and air bearings. These alternative structures are known in the art and need not be described in exhaustive detail in furtherance of brevity.

By way of example, the baseplate 180 comprises a solid rectangular cuboid that may be fabricated from a solid block of aluminum and has a pair of through holes 182 located near respective upper corners on opposing surfaces. More specifically, the through holes 182 extend between opposing longitudinal surfaces 184, where the longitudinal opposed surfaces embody the dominant longitudinal dimension of the baseplate 180. One of the connecting surfaces 188, 190 of the baseplate 180, which spans the surfaces 184, 186 through which the holes 182 extend, has four cavities 196 formed therein. A series of threaded cavities 198 are formed through the second connecting surface 190 and aligned to overlap respective openings 112 of the platform 106 and are configured to receive fasteners 200 that mount the baseplate 180 to the platform. The second set of cavities 196 is formed through the first connecting surface 188 to expose the through holes 182. In exemplary form, the cavities 196 are bounded by opposing planar surfaces 204 connected by a curved surface 206. As will be discussed in more detail hereafter, the dimensions of the cavities 198 allow pivotal motion of the levers 162 so that the sled 150 may be repositioned with respect to the baseplate 180.

In exemplary form, the sled 150 is repositionable with respect to the baseplate 180, which is stationary with respect to the platform 106. In particular, the sled 150 is pivotally repositionable with respect to the baseplate 180 by way of a connection to the levers 162. Each lever 162 comprises a pair of oblong, planar surfaces 210 that are spanned by constant height peripheral surface 212. In this exemplary embodiment, the levers may be fabricated from aluminum. The peripheral surface 212 includes a pair of planar surface segments that are spanned by arcuate surfaces having a semi-circular profile. Each oblong planar surface 212 is identically sized and includes a pair of holes 174 that interconnect to counterpart holes 158, 182 to delineate a pair of cylindrical channels that extend through the levers 162 and respectively through the sled 150 and baseplate 180. Each of these channels is sized to receive a fastener 160, 216, such as a shoulder bolt. In exemplary form, respective fasteners 216 extend through baseplate holes 182 and extend through respective lower holes 214 of the levers 162, while a first end of each lever 162 is positioned within respective cavities 198 of the baseplate 180, thereby allowing the lever 162 to pivot with respect to the baseplate 180 and around a collar 218 of the fasteners 216. Similarly, respective fasteners 160 extend through sled holes 158 and extend through respective upper holes 158 of the levers 162 while a second end of each lever 162 is positioned within respective cavities 166 of the sled 150, thereby allowing the lever 162 to pivot with respect to the sled 150 and around a collar 220 of the fasteners 160. In this exemplary embodiment, the underside of the sled 150 includes a rounded rectangular recess 230 that outlines a rounded rectangular plateau 232 of the baseplate 180. As will be discussed in more detail hereafter, relative motion between the sled 150 and baseplate 180 is indicative of forces applied to a test conduit 240 resulting from resistance to insertion or withdrawal of a medical device 300, 302 into or from a test conduit 240.

In exemplary form, the test conduit 240 is secured to the sled 150 and comprises a tortuous, hollow pathway that may be shaped to replicate or resemble a patient bodily channel. By way of example, the test conduit 240 may be fabricated from any number of materials such as, without limitation, polymers, ceramics (including glass), metals, composites, and any other material capable of delineating a hollow pathway. By way of further example, the test conduit 240 may embody a constant geometric profile (e.g., a circular profile) or may have profiles that vary along the length of the pathway. Opposing ends of the test conduit 240 are open to provide for egress of medical instruments 300, 302 such as, without limitation, medical catheters. In order to secure the test conduit 240 to the sled 150, retention caps 246 are fastened to the sled 150. More specifically, each of the retention caps 246 (that may be fabricated from aluminum) and the towers 152, 154 includes respective arcuate depressions 248, 250 that are configured to circumscribe terminal portions of the test conduit 240 when the retention caps are mounted to the towers. The arcuate depressions 248, 250 have a profile (e.g., semicircular) matching the outer profile of the test conduit 240 in order to hold the test conduit in position with respect to the sled 150 when the caps 246 are in place. In order to mount the caps 246 to the sled 150, and thereby sandwich the test conduit 240 between the caps and sled, each cap includes two through holes 252 sized to receive corresponding threaded fasteners 254 that extend into corresponding threaded cavities 256 on the top of the towers 152, 154. In this fashion, inserting the threaded fasteners 254 through the holes 252 and into engagement with the threaded cavities 256 and torquing the fasteners is operative to mount the caps 246 to the sled 150 and sandwich the test conduit therebetween so that relative motion between the test conduit, sled, and caps is minimized or eliminated. In this fashion, after the test conduit 240 is secured in place, forces applied to the test conduit 240 result in the load cell 144 generating outputs that are communicated to the computer 104 via the communication link 103.

Referring back to FIG. 1, the exemplary force analytic system 100 may be utilized to provide quantitative data as to the force required to cause insertion or withdrawal of a device through the test conduit 240. By way of example, the device may comprise a medical device. But it should also be understood, however, that devices and articles other than medical devices may tested to evaluate insertion and withdrawal forces. These other exemplary devices and articles that may be tested include, without limitation, cables, wires, and any other substrate for which insertion and withdrawal forces are sought to be determined as being within the scope of the instant disclosure.

As mentioned previously, the test conduit 240 may be fabricated from any number of materials and have any number of shapes and cross-sections. Regardless of the shape and material of the test conduit 240, presuming the same test conduit is utilized to standardize the data received from the load cell 144 across multiple medical devices tested, the exemplary force analytic system 100 generates force data (in dynes) as a function of time when one inserts and/or withdraws a medical device 300, 302 with respect to the test conduit. A more detailed discussion of an exemplary processing sequence for utilizing the exemplary force analytic system 100 follows.

Figure 7:
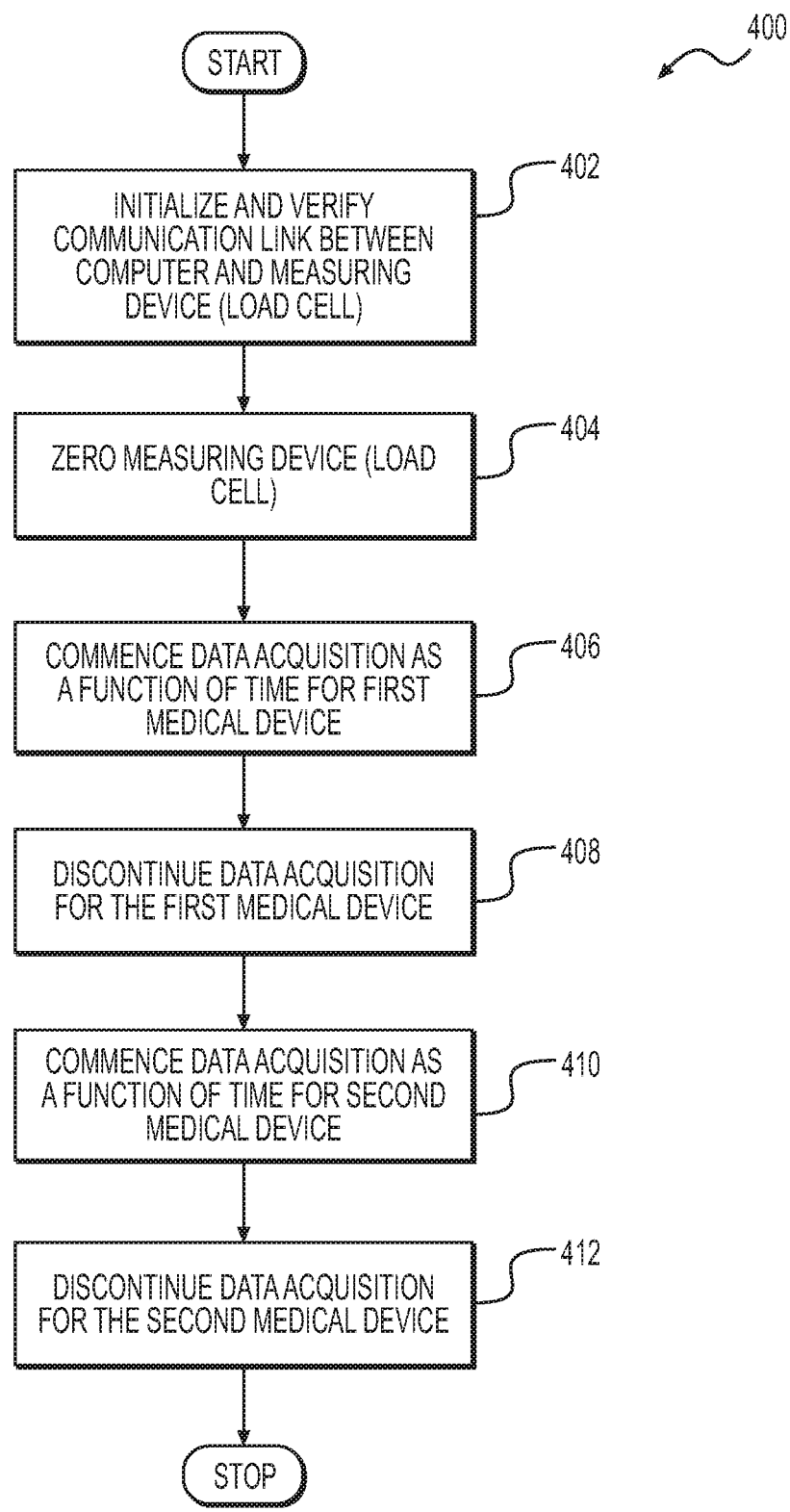
FIG. 7 is an exemplary process flow diagram for a testing a medical device in accordance with the instant disclosure.

Referring to FIG. 7, as an initial matter, utilizing the exemplary force analytic system 100 presumes the measuring device 102 is fully assembled to allow the sled 150 to be repositioned with respect to the baseplate 180. Likewise, it is presumed that the test conduit 240 is secured to the sled 150 so that relative movement between the test conduit and sled is avoided. Moreover, it is presumed that the load cell 144 is communicatively coupled to the computer 104 and that the computer is programmed with a data acquisition program utilizing the output signals from the load cell to calculate a resultant force. With these presumptions in place, utilizing the exemplary force analytic system 100 will be described in exemplary form.

For purposes of explanation only, the following exemplary description of a process 400 for using the force analytic system 100 makes use of two or more catheters as the tested medical devices 300, 302. Those skilled in the art will fully understand that medical devices 300, 302 other than catheters may be tested in accordance with the instant disclosure such as, without limitation, guidewires, access sheaths, baskets, snares, stents, stylets, and scopes. Accordingly, when the following exemplary process refers to a catheter, it should be understood that this reference refers generally to any medical device 300, 302.

Before any medical device 300, 302 is tested, a prefatory step 402 includes initializing and verifying the communication link 103 between the load cell 144 and the computer 104 is operative. In order to do so, one may establish a wired or wireless data communication link 103 between the computer 104 and load cell 144 so that electrical signals output from the load cell are communicated to the computer and utilized by the computer to compute force acting on the load cell 144. Post communication link 103 initialization and verification, the process includes a zeroing step 404 to ensure signals from the load cell 144, transmitted via the communication link 103, to the computer 104 account for a static state (i.e., to zero the reading from the load cell 144) where no medical insertion device 300, 302 is inserted into or withdrawn from the test conduit 240. In other words, the load cell 144 may be sending signals to the computer 104, but these signals may represent forces that are constantly acting on the load cell and need to be factored out during the insertion force testing sequence. After zeroing the signals from the load cell 144 to represent a static state, the force testing portion of the process 400 may commence.

As part of this exemplary embodiment 100 and testing process 400, the computer 104 includes a data acquisition program operative to record electrical signals from the load cell 144 (via the communication link 103) and utilizes these signals to compute applied force. The computed applied force is representative of the amount of force at a given time required to cause the medical device 300, 302 to traverse the test conduit 240, whether the traversal is the result of insertion into or withdrawal from the test conduit. As part of the recordation of these electrical signals from the load cell 144, the computer 104 includes an internal clock communicating with the data acquisition program to allow for data acquisition as a function of time. Specifically, the data acquisition program of the computer 104 includes a graphical user interface component 107 that may be displayed on a computer monitor 109 or any associated electronic visual display communicatively coupled to the computer 104.

Figure 8:
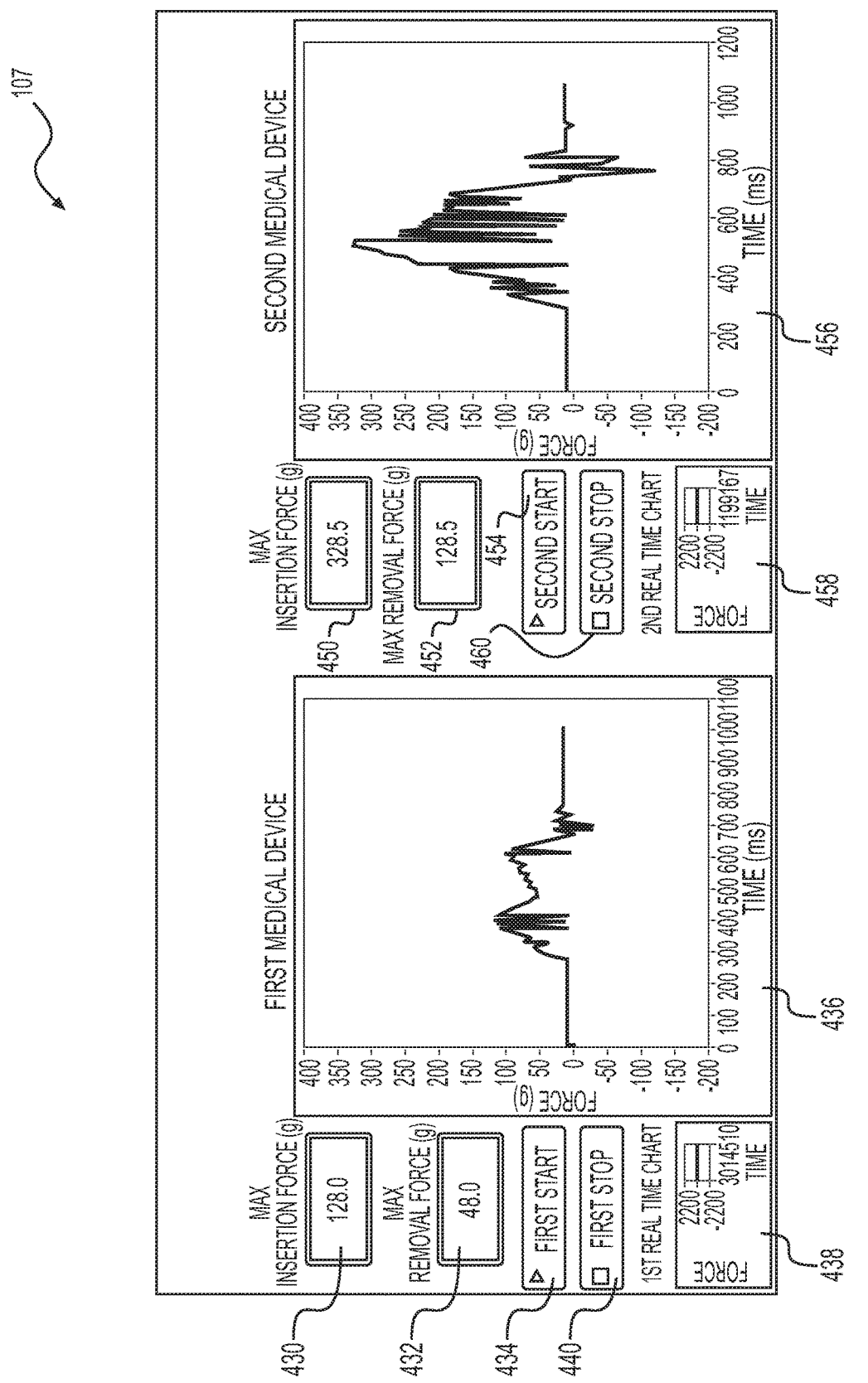
FIG. 8 is a screen shot of an exemplary graphical user interface in accordance with the instant disclosure.

Referring to FIG. 8, an exemplary graphical user interface (GUI) component 107 may include a first numerical display 430 providing data representative of the maximum insertion force of a first tested medical device 300 throughout the testing process 400. A second numerical display 432 of the GUI component 107 may provide data representative of the maximum removal/withdrawal force of the first tested medical device 300 throughout the testing process 400. The GUI component 107 may also include a button 434 that may be activated using a cursor (via a mouse or touchpad) associated with the computer 104 to commence a data acquisition step 406. Data is acquired from the load cell 144 as a function of time while a user inserts the tested medical device 300 (e.g., catheter) into the open end of the test conduit opposite the load cell 144. As the first medical device 300 is inserted into the test conduit 240, a first graphical display 436 may depict a continuous series of data points reflecting how insertion force (measured in dynes) changes with respect to time (measured in milliseconds). In exemplary form, the data points are displayed on the graphical display 436 in real-time. Given the variance in scale that may be depicted as part of the graphical display 436 to account for the test time and maximum forces measured, which may make precise reading of the first graphical display 436 more difficult, the GUI component 107 may also include a first magnified view window 438 that may display in real-time a running and changing measured force as a function of time for a snippet range (approximately a 200 millisecond band) across the testing total time of the first tested medical device 300. This first magnified view window 438 provides the advantage of more precise, real-time viewing of the measured force as a function of time. Depending upon the desired insertion length chosen by a user for the first medical device 300 tested, the insertion may be stopped and withdrawal of the first medical device commenced. Throughout the testing process 400, the data acquisition program tracks/records the greatest insertion force calculated and the greatest withdrawal forced calculated. These two maximum forces are updated in real-time in the respective numerical displays 430, 432. Data continues to be displayed on the displays/windows 430-438 and is updated until a stop button 440 associated with the GUI component 107 is activated (using a cursor associated with the computer 104) to conclude data acquisition 408 associated with the first tested medical device 300.

As is depicted in the first graphical display 436, positive calculated numerical forces are indicative of insertion forces needed to direct the first tested medical device 300 through the test conduit 240 in a direction toward the load cell 144. Conversely, negative calculated numerical forces are indicative of withdrawal forces needed to direct the first tested medical device 300 through the test conduit 240 in a direction away from the load cell 144. A zero calculated numerical force represents a state where either the first tested medical device 300 is stationary, or where the medical device is moving along the test conduit 240 without measurable resistance, or where the medical device experiences rebound forces resulting from linear compression of the device itself.

As is reflected by the first graphical display 436, the first medical device 300 was inserted into the test conduit 240 and began applying a force to the test conduit 240 and load cell 144 at approximately 550 milliseconds and continued applying some positive force until reaching 1000 milliseconds. During this insertion traversal, the maximum insertion force calculated is 128 dynes, which is displayed in the first numerical display 430. After reaching maximum insertion (or a predetermined insertion location or length), the medical device 300 may be withdrawn from the test conduit 240. As is reflected in the first graphical display 436, withdrawal of the first medical device 300 took approximately 100 milliseconds, with a maximum withdrawal force calculated as −48 dynes. This maximum withdrawal force is displayed in the second numerical display 432 as the absolute value of the calculated maximum withdrawal force. Post completion of the testing and withdrawal of the first medical device 300, the testing of the second medical device may commence at step 410.

The exemplary graphical user interface (GUI) component 107 may include a third numerical display 450 providing data representative of the maximum insertion force of a second tested medical device 302 throughout the testing process 400. A fourth numerical display 452 of the GUI component 107 may provide data representative of the maximum removal/withdrawal force of the second tested medical device 302 throughout the testing process 400. The GUI component 107 may also include a comparative button 454 that may be activated using a cursor (via a mouse or touchpad) associated with the computer 104 to commence the data acquisition step 410 for the second medical device 302.

Data is acquired from the load cell 144 as a function of time while a user inserts the tested medical device 302 (e.g., catheter) into the open end of the test conduit opposite the load cell 144. As the second medical device 302 is inserted into the test conduit 240, a second graphical display 456 depicts a continuous series of data points reflecting how insertion force (measured in dynes) changes with respect to time (measured in milliseconds). In exemplary form, the data points are displayed on the graphical display 456 in real-time. Given the variance in scale that may be depicted as part of the graphical display to account for the test time and maximum forces measured, which may make precise reading of the second graphical display 456 more difficult, the GUI component 107 may also include a second magnified view window 458 that may display in real-time a running and changing calculated force as a function of time for a snippet range (approximately a 200 millisecond band) across the testing total time of the second tested medical device 302. This second magnified view window 458 provides the advantage of more precise, real-time viewing of the measured force as a function of time. Depending upon the desired insertion length chosen by a user for the second medical device 302 tested, the insertion may be stopped and withdrawal of the second medical device commenced. Throughout the testing process 400, the data acquisition program tracks/records the greatest insertion force calculated and the greatest withdrawal forced calculated for the second medical device 302. These two maximum forces are updated in real-time in the respective numerical displays 450, 452. Data continues to be displayed on the displays/windows 450-458 and updated until a comparative stop button 460 associated with the GUI component 107 is activated (using a cursor associated with the computer 104) to conclude data acquisition 412 associated with the second tested medical device 302.

As is depicted in the second graphical display 456, positive calculated numerical forces are indicative of insertion forces needed to direct the second tested medical device 302 through the test conduit 240 in a direction toward the load cell 144. Conversely, negative calculated numerical forces are indicative of withdrawal forces needed to direct the second tested medical device 302 through the test conduit 240 in a direction away from the load cell 144. A zero calculated numerical force represents a state where either the second tested medical device 302 is stationary, or where the medical device is moving along the test conduit 240 without measurable resistance, or where the medical device experiences rebound forces resulting from linear compression of the device itself. As is reflected by the second graphical display 456, the second medical device 302 was inserted into the test conduit 240 and began applying a force to the test conduit and load cell 144 at approximately 350 milliseconds and continued applying some positive force until reaching 825 milliseconds. During this insertion traversal, the maximum insertion force calculated was 328.5 dynes, which is displayed in the third numerical display 450. After reaching maximum insertion (or a predetermined insertion location or length), the medical device 302 may be withdrawn from the test conduit 240. As is reflected in the second graphical display 456, withdrawal of the second medical device 302 took approximately 150 milliseconds, with a maximum withdrawal force being calculated as −128.5 dynes. This maximum withdrawal force is displayed in the fourth numerical display 452 as the absolute value of the calculated maximum withdrawal force for the second medical device 302. Post completion of the withdrawal of the second medical device 302 from the test conduit 240, the process 400 is concluded.

It should be noted that the foregoing fasteners may be fabricated from any number of materials including, without limitation, metals such aluminum, steel, titanium, and steel alloys. It should also be noted that while many of the foregoing components are described as being fabricated from blocks of aluminum (and subsequently machined), it is also within the scope of the invention for these materials to be fabricated from materials other than aluminum such as, without limitation, polymers, composites, and metals and metal alloys other than pure aluminum.

Following from the above description, it should be apparent to those of ordinary skill in the art that, while the methods, devices, and systems herein described constitute exemplary embodiments of the present disclosure, the embodiments described herein are not limited to any precise embodiment and that changes may be made to such embodiments without departing from the scope of the disclosure as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present exemplary embodiments may exist even though they may not have been explicitly discussed herein.

What is claimed is:

1. A force measuring system comprising:
 a tortuous conduit having a predetermined path operatively coupled to a transducer; and,
 a computer communicatively coupled to the transducer, the computer programmed to utilize signals output from the transducer to calculate forces acting on the transducer, the computer programmed to support a graphical user interface for displaying the calculated forces.

2. The measuring system of claim 1, wherein the transducer comprises a load cell.

3. The measuring system of claim 1, wherein:
 a first portion of the transducer is mounted to a base comprising a stationary support; and,
 a second portion of the transducer is mounted to a sled repositionably mounted to the base.

4. The measuring system of claim 3, wherein:
 the tortuous conduit is removably mounted to the sled; and, the sled includes a pair of upstanding arms that cooperatively engage a retention cap to selectively mount the tortuous conduit to the sled.

5. The measuring system of claim 3, wherein the sled is at least one of pivotally repositionable and slidably repositionable with respect to the base.

6. The measuring system of claim 5, wherein:
the sled is pivotally repositionable with respect to the base; and,
a lever operatively couples the sled and the base and provides for the sled to pivot with respect to the base.

7. The measuring system of claim 6, wherein the lever comprises a plurality of levers.

8. The measuring system of claim 6, wherein:
at least one of the sled and the base includes a cavity into which the lever is at least partially inserted;
the lever includes a pair of hollowed areas configured to receive cylindrical pins;
the sled includes a sled opening sized to receive a first one of the cylindrical pins; and,
the base includes a base opening sized to receive a second one of the cylindrical pins.

9. The measuring system of claim 5, wherein:
the sled is slidably repositionable with respect to the base; and,
a slide operatively couples the sled and the base and provides for the sled to slide with respect to the base.

10. The measuring system of claim 1, wherein:
the transducer interposes the tortuous conduit and a stationary support; and,
the transducer is mounted to the stationary support.

11. A process for comparing at least one of insertion and withdrawal forces associated with at least two devices, the process comprising:
inserting a first device into a tortuous conduit having a predetermined path;
recording insertion data indicative of insertion forces applied by the first device traveling in a first direction in the tortuous conduit;
withdrawing the first device from the tortuous conduit;
recording withdrawal data indicative of withdrawal forces applied by the first device traveling in a second direction in the tortuous conduit, where the second direction is generally opposite the first direction;
repeating the foregoing steps by replacing the first device with a second device; and,
comparing the insertion data and withdrawal data between at least the first and second devices.

12. The process of claim 11, wherein:
the tortuous conduit is rigidly mounted to a load cell;
the load cell is configured to output signals having a magnitude proportional to a force applied to the tortuous conduit; and,
the load cell is communicatively coupled to a programmed computer utilizing the signals and calculating the insertion forces and calculating the withdrawal forces.

13. The process of claim 12, wherein:
the programmed computer supports a graphical user interface; and,
the graphical user interface displays the insertion forces and the withdrawal forces.

14. The process of claim 13, wherein:
the insertion forces include a maximum insertion force;
the withdrawal forces include a maximum withdrawal force;
the graphical user interface displays the maximum insertion force and the maximum insertion force as part of a graph depicting force as a function of time; and,
the graphical user interface displays a separate graph for the first device and the second device.

15. The process of claim 14, wherein:
the graphical user interface also displays the maximum insertion force separate from the graph;
the graphical user interface also displays the maximum withdrawal force separate from the graph; and,
the graphical user interface displays a separate reading for the maximum withdrawal force and the maximum insertion force for the first device and the second device.

16. The process of claim 14, wherein:
the insertion forces are displayed on the graphical user interface in real-time; and,
the withdrawal forces are displayed on the graphical user interface in real-time.

17. The process of claim 13, wherein:
the graphical user interface includes a button to be clicked for initiating recordation of the insertion data; and,
the graphical user interface includes a button to be clicked for concluding recordation of the withdrawal data.

18. The process of claim 17, wherein the button initiating recordation of the insertion data is the same as the button concluding recordation of the withdrawal data.

19. The process of claim 17, wherein graphical user interface includes a separate button initiating recordation of the insertion data for the first device and a separate button for concluding recordation of the withdrawal data for the second device.

20. The process of claim 11, wherein the tortuous conduit is representative of a bodily conduit the first and second devices would traverse when used during a medical procedure.

21. The process of claim 11, wherein the first and second devices comprise a first catheter and a second catheter.

22. The process of claim 11, wherein the tortuous conduit is linked to a transducer mounted to a stationary support.

* * * * *